US007041806B2

(12) United States Patent
Tessier-Lavigne et al.

(10) Patent No.: US 7,041,806 B2
(45) Date of Patent: May 9, 2006

(54) NETRIN RECEPTORS

(75) Inventors: Mark Tessier-Lavigne, San Francisco, CA (US); E. David Leonardo, San Francisco, CA (US); Lindsay Hinck, San Francisco, CA (US); Masayuki Masu, San Francisco, CA (US); Kazuko Keino-Masu, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 194 days.

(21) Appl. No.: 10/256,702

(22) Filed: Sep. 27, 2002

(65) Prior Publication Data

US 2003/0059859 A1 Mar. 27, 2003

Related U.S. Application Data

(60) Continuation of application No. 09/933,261, filed on Aug. 20, 2001, which is a division of application No. 09/306,902, filed on May 7, 1999, now Pat. No. 6,277,585, which is a division of application No. 08/808,982, filed on Feb. 19, 1997, now Pat. No. 5,939,271.

(51) Int. Cl.
*C07K 16/00* (2006.01)
*C12P 21/08* (2006.01)
*A61K 39/395* (2006.01)
*A61K 39/40* (2006.01)
*G01N 33/53* (2006.01)

(52) U.S. Cl. ............... 530/387.9; 530/387.1; 530/388.1; 530/388.22; 530/389.1; 530/391.3; 424/139.1; 424/141.1; 424/143.1; 424/178.1; 435/7.1

(58) Field of Classification Search ............. 530/387.1, 530/387.9, 387.3, 388.1, 388.15; 424/130.1, 424/139.1; 435/7.1, 4
See application file for complete search history.

(56) References Cited

FOREIGN PATENT DOCUMENTS

| WO | 93/16178 | 8/1993 |
|---|---|---|
| WO | 97/14424 | 4/1997 |

OTHER PUBLICATIONS

Culotti JG. Database Medline on Dialog, US National Library of Medicine, (Bethesda, MD, USA), No. 08202090 95037661. 'Axon Guidance mechanisms in Caenorhabditits elegans', Current Opinion in Genetics and Developments, abstract, Aug. 1994, vol. 4, No. 4, pp. 587-595.
Hinck, L. et al. "Vertebrate homologs of C. elegans UNC-5 are candidate netrin receptors." Soc. For Neuroscience Abstracts, vol. 22, No. 1-3, 1996 p. 1470.
Database EMBL; ID: HS163137; AC: R67163, Jun. 4, 1995 "yh08c06.r2 Soares infant brain 1NIB Homo sapiens clone IMAGE:42591 5', mRNA sequence."
Database EMBL; ID: HS716233; AC: H43716, Nov. 17, 1995 "yo80g05.s1 Soares adult brain N2b4HB55Y Homo sapiens cDNA clone IMAGE: 184280 3', mRNA sequence".
Aekerman et al. Nature 1997, 386:838-42.
Leonardo, E. David et al: "Vertebrate homologues of C. elegans UNC-5 are candidate netrin receptors." Nature (London), vol. 386, No. 6627, Apr. 24, 1997, pp. 833-838.
Leung-Hagesteijn et al., Cell, 71:289-99, 1992.

*Primary Examiner*—Olga N. Chernyshev
(74) *Attorney, Agent, or Firm*—Townsend and Townsend and Crew LLP

(57) ABSTRACT

The invention provides methods and compositions relating to vertebrate UNC-5 proteins which function as receptor proteins for netrins, a family of cell guidance proteins. The proteins may be produced recombinantly from transformed host cells from the disclosed vertebrate UNC-5 encoding nucleic acid or purified from human cells. The invention provides specific hybridization probes and primers capable of specifically hybridizing with the disclosed vertebrate unc-5 gene, vertebrate UNC-5-specific binding agents such as specific antibodies, and methods of making and using the subject compositions in diagnosis, therapy and in the biopharmaceutical industry.

14 Claims, No Drawings

NETRIN RECEPTORS

CROSS-REFERENCE TO RELATED APPLICATIONS

This application is a continuation of and claims priority under 35 U.S.C. § 120 to U.S. Ser. No. 09/933,261, filed Aug. 20, 2001, which is a divisional of and claims priority to U.S. Ser. No. 09/306,902, filed May 7, 1999, U.S. Pat. No. 6,277,585, which is a divisional of and claims priority to U.S. Ser. No. 08/808,982, filed Feb. 19, 1997, Pat. No. 5,939,271, which are incorporated herein by reference.

The research carried out in the subject application was supported in part by grants from the National Institutes of Health. The government may have rights in any patent issuing on this application.

INTRODUCTION

1. Field of the Invention

The field of this invention is proteins which regulate vertebrate cell guidance.

2. Background

In the developing nervous system, migrating cells and axons are guided to their targets by cues in the extracellular environment. The netrins are a family of phylogenetically-conserved guidance cues that can function as diffusible attractants and repellents for different classes of cells and axons[1-10]. Recent studies in vertebrates, insects and nematodes have implicated members of the DCC subfamily of the immunoglobulin (Ig) superfamily as receptors involved in migrations toward netrin sources[6,11-13]. The mechanisms that direct migrations away from netrin sources (presumed repulsions) are less well understood. In Caenorhabditis elegans, loss of unc-5 (which encodes the transmembrane protein UNC-5[14]) function causes defects in these migrations[15,16], and ectopic expression of unc-5 in some neurons can redirect their axons away from a netrin source[17]. However, the relationship between UNC-5 and the netrins has not been defined. We disclose herein vertebrate homologues of the C. elegans UNC-5, which define a novel subfamily of the Ig superfamily, and whose mRNAs show prominent expression in various classes of differentiating neurons and we disclose that these vertebrate UNC-5 homologues are vertebrate netrin-binding proteins.

SUMMARY OF THE INVENTION

The invention provides methods and compositions relating to vertebrate UNC-5 proteins. related nucleic acids, and protein domains thereof having vertebrate UNC-5-specific activity. The proteins may be produced recombinantly from transfected host cells from the subject vertebrate UNC-5 encoding nucleic acids or purified from vertebrate cells. The invention provides isolated vertebrate unc-5 hybridization probes and primers capable of specifically hybridizing with the disclosed vertebrate unc-5 genes, vertebrate UNC-5-specific binding agents such as specific antibodies, and methods of making and using the subject compositions in diagnosis (e.g. genetic hybridization screens for vertebrate unc-5 transcripts), therapy (e.g. gene therapy to modulate vertebrate unc-5 gene expression) and in the biopharmaceutical industry (e.g. as immunogens, reagents for modulating cell guidance, reagents for screening chemical libraries for lead pharmacological agents, etc.).

DETAILED DESCRIPTION OF THE INVENTION

The nucleotide sequences of natural unc5h-1 cDNAs from rat and human are shown as SEQ ID NOS:1 and 2, respectively; and the conceptual translates are shown as SEQ ID NOS: 5 and 6, respectively. The nucleotide sequences of natural unc5h-2 cDNAs from rat and human are shown as SEQ ID NOS:3 and 4, respectively; and the conceptual translates are shown as SEQ ID NOS:7 and 8, respectively. The vertebrate UNC-5 proteins of the invention include incomplete translates of SEQ ID NOS:1, 2, 3 and 4 and deletion mutants of SEQ ID NOS:5, 6, 7 and 8, which translates and deletion mutants have vertebrate UNC-5-specific amino acid sequence and assay-discernable vertebrate UNC-5-specific binding specificity or function. Such active vertebrate UNC-5 deletion mutants, vertebrate UNC-5 peptides or protein domains comprise at least about 8, preferably at least about 12, more preferably at least about 24 consecutive residues of SEQ ID NO:5, 6, 7 or 8. For examples, vertebrate UNC-5 protein domains identified below are shown to provide protein-binding domains which are identified in and find use, inter alia, in solid-phase binding assays as described below.

Vertebrate UNC-5-specific activity or function may be determined by convenient in vitro, cell-based, or in vivo assays: e.g. in vitro binding assays, cell culture assays, in animals (e.g. gene therapy, transgenics, etc.), etc. Binding assays encompass any assay where the molecular interaction of a vertebrate UNC-5 protein with a binding target is evaluated. The binding target may be a natural extracellular binding target such as a netrin protein, or other regulator that directly modulates vertebrate UNC-5 activity or its localization; or non-natural binding target such a specific immune protein such as an antibody, or an vertebrate UNC-5 specific agent such as those identified in screening assays such as described below. Vertebrate UNC-5-binding specificity may assayed by binding equilibrium constants (usually at least about $10^7 M^{-1}$, preferably at least about $10^8 M^{-1}$, more preferably at least about $10^9 M^{-1}$), by the ability of the subject protein to function as negative mutants in vertebrate UNC-5-expressing cells, to elicit vertebrate UNC-5 specific antibody in a heterologous mammalian host (e.g a rodent or rabbit), etc. In any event, the vertebrate UNC-5 binding specificity of the subject vertebrate UNC-5 proteins necessarily distinguishes C. elegans UNC-5.

The claimed vertebrate UNC-5 proteins are isolated or pure: an "isolated" protein is unaccompanied by at least some of the material with which it is associated in its natural state, preferably constituting at least about 0.5%, and more preferably at least about 5% by weight of the total protein in a given sample and a pure protein constitutes at least about 90%, and preferably at least about 99% by weight of the total protein in a given sample. The vertebrate UNC-5 proteins and protein domains may be synthesized, produced by recombinant technology, or purified from mammalian, preferably human cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, New York) or that are otherwise known in the art.

The invention provides natural and non-natural vertebrate UNC-5-specific binding agents, methods of identifying and making such agents, and their use in diagnosis, therapy and pharmaceutical development. For example, vertebrate UNC-5-specific agents are useful in a variety of diagnostic and therapeutic applications. Vertebrate UNC-5-specific binding agents include vertebrate UNC-5-specific ligands, such as netrins, and somatically recombined protein receptors like specific antibodies or T-cell antigen receptors (see, e.g. Harlow and Lane (1988) Antibodies, A Laboratory Manual, Cold Spring Harbor Laboratory, including Chapter 6: Monoclonal Antibodies) and other natural binding agents identified with assays such as one-, two- and three-hybrid screens, non-natural binding agents identified in screens of chemical libraries such as described below, etc. For diagnostic uses, the binding agents are frequently labeled, such as with fluorescent, radioactive, chemiluminescent, or other easily detectable molecules, either conjugated directly to the binding agent or conjugated to a probe specific for the binding agent. Agents of particular interest modulate vertebrate UNC-5 function, e.g. vertebrate UNC-5-dependent cell guidance; for example, isolated cells, whole tissues, or individuals may be treated with a vertebrate UNC-5 binding agent to activate, inhibit, or alter vertebrate UNC-5-dependent cell guidance or function.

The invention provides UNC-5 related nucleic acids, which find a wide variety of applications including use as translatable transcripts, hybridization probes, PCR primers, diagnostic nucleic acids, etc.; use in detecting the presence of unc-5 genes and gene transcripts and in detecting or amplifying nucleic acids encoding additional unc-5 homologs and UNC-5 structural analogs. The subject nucleic acids are of synthetic/non-natural sequences and/or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. Nucleic acids comprising the nucleotide sequence of SEQ ID NO:1, 2, 3 or 4 or fragments thereof, contain such sequence or fragment at a terminus, immediately flanked by a sequence other than that which it is joined to on a natural chromosome, or flanked by a native flanking region fewer than 10 kb, preferably fewer than 2 kb, which is at a terminus or is immediately flanked by a sequence other than that which it is joined to on a natural chromosome. While the nucleic acids are usually RNA or DNA, it is often advantageous to use nucleic acids comprising other bases or nucleotide analogs to provide modified stability, etc.

The amino acid sequences of the disclosed vertebrate UNC-5 proteins are used to back-translate vertebrate UNC-5 protein-encoding nucleic acids optimized for selected expression systems (Holler et al. (1993) Gene 136, 323–328; Martin et al. (1995) Gene 154, 150–166) or used to generate degenerate oligonucleotide primers and probes for use in the isolation of natural vertebrate UNC-5-encoding nucleic acid sequences ("GCG" software, Genetics Computer Group, Inc, Madison Wis.). vertebrate UNC-5-encoding nucleic acids used in vertebrate UNC-5-expression vectors and incorporated into recombinant host cells, e.g. for expression and screening, transgenic animals, e.g. for functional studies such as the efficacy of candidate drugs for disease associated with vertebrate UNC-5-modulated transcription, etc.

The invention also provides nucleic acid hybridization probes and replication/amplification primers having a vertebrate UNC-5 cDNA specific sequence contained in SEQ ID NO:1, 2, 3 or 4 and sufficient to effect specific hybridization thereto (i.e. specifically hybridize with the corresponding SEQ ID NO:1, 2, 3 or 4 in the presence of C. elegans unc-5 cDNA). Such primers or probes are at least 12, preferably at least 24, more preferably at least 36 and most preferably at least 96 bases in length. Demonstrating specific hybridization generally requires stringent conditions, for example, hybridizing in a buffer comprising 30% formamide in 5×SSPE (0.18 M NaCl, 0.01 M NaPO$_4$, pH7.7, 0.001 M EDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C. with 0.2×SSPE buffer at 42° C. vertebrate UNC-5 cDNA homologs can also be distinguished from other protein using alignment algorithms, such as BLASTX (Altschul et al. (1990) Basic Local Alignment Search Tool, J Mol Biol 215, 403–410).

Vertebrate unc-5 hybridization probes find use in identifying wild-type and mutant vertebrate unc-5 alleles in clinical and laboratory samples. Mutant alleles are used to generate allele-specific oligonucleotide (ASO) probes for high-throughput clinical diagnoses. Therapeutic vertebrate UNC-5 nucleic acids are used to modulate cellular expression or intracellular concentration or availability of active vertebrate UNC-5. For example, vertebrate UNC-5 nucleic acids are also used to modulate cellular expression or intracellular concentration or availability of active vertebrate UNC-5 protein. Vertebrate UNC-5 inhibitory nucleic acids are typically antisense: single-stranded sequences comprising complements of the disclosed natural vertebrate UNC-5 coding sequences. Antisense modulation of the expression of a given vertebrate UNC-5 protein may employ antisense nucleic acids operably linked to gene regulatory sequences. Cells are transfected with a vector comprising a vertebrate UNC-5 sequence with a promoter sequence oriented such that transcription of the gene yields an antisense transcript capable of binding to endogenous vertebrate UNC-5 encoding mRNA. Transcription of the antisense nucleic acid may be constitutive or inducible and the vector may provide for stable extrachromosomal maintenance or integration. Alternatively, single-stranded antisense nucleic acids that bind to genomic DNA or mRNA encoding a given vertebrate UNC-5 protein may be administered to the target cell, in or temporarily isolated from a host, at a concentration that results in a substantial reduction in expression of the targeted protein. An enhancement in vertebrate UNC-5 expression is effected by introducing into the targeted cell type vertebrate UNC-5 nucleic acids which increase the functional expression of the corresponding gene products. Such nucleic acids may be vertebrate UNC-5 expression vectors, vectors which upregulate the functional expression of an endogenous allele, or replacement vectors for targeted correction of mutant alleles. Techniques for introducing the nucleic acids into viable cells are known in the art and include retroviral-based transfection, viral coat protein-liposome mediated transfection, etc.

The invention provides efficient methods of identifying agents, compounds or lead compounds for agents active at the level of a vertebrate UNC-5 modulatable cellular function. Generally, these screening methods involve assaying for compounds which modulate vertebrate UNC-5 interaction with a natural vertebrate UNC-5 binding target. A wide variety of assays for binding agents are provided including labeled in vitro protein-protein binding assays, immunoassays, cell based assays, animal based assay, etc. Preferred methods are amenable to automated, cost-effective high throughput screening of chemical libraries for lead compounds. Such libraries encompass candidate agents of numerous chemical classes, though typically they are organic compounds; preferably small organic compounds and are obtained from a wide variety of sources including libraries of synthetic or natural compounds. Identified agents find use in the pharmaceutical industries for animal and human trials; for example, the agents may be derivatized and rescreened in in vitro and in vivo assays to optimize activity and minimize toxicity for pharmaceutical development.

In vitro binding assays employ a mixture of components including vertebrate UNC-5 protein, which may be part of a fusion product with another peptide or polypeptide, e.g. a tag for detection or anchoring, etc. The assay mixtures comprise a natural extracellular vertebrate UNC-5 binding target, such as a netrin. While native binding targets may be used, it is frequently preferred to use portions (e.g. peptides) thereof so long as the portion provides binding affinity and avidity to the subject vertebrate UNC-5 protein conveniently measurable in the assay. The assay mixture also comprises a candidate pharmacological agent and typically, a variety of other reagents such as salts, buffers, neutral proteins, e.g. albumin, detergents, protease inhibitors, nuclease inhibitors, antimicrobial agents, etc. The mixture components can be added in any order that provides for the requisite bindings and incubations may be performed at any temperature which facilitates optimal binding. The mixture is then incubated under conditions whereby, but for the presence of the candidate pharmacological agent, the vertebrate UNC-5 protein specifically binds the cellular binding target, portion or analog with a reference binding affinity. Incubation periods are likewise selected for optimal binding but also minimized to facilitate rapid, high-throughput screening.

After incubation, the agent-biased binding between the vertebrate UNC-5 protein and one or more binding targets is detected. A separation step is often initially used to separate bound from unbound components. Separation may be effected by precipitation (e.g. TCA precipitation, immunoprecipitation, etc.), immobilization (e.g on a solid substrate), etc., followed by washing by, for examples, membrane filtration, gel chromatography (e.g. gel filtration, affinity, etc.). One of the components usually comprises or is coupled to a label. The label may provide for direct detection such as radioactivity, luminescence, optical or electron density, etc. or indirect detection such as an epitope tag, an enzyme, etc. A variety of methods may be used to detect the label depending on the nature of the label and other assay components, e.g. through optical or electron density, radiative emissions, nonradiative energy transfers, etc. or indirectly detected with antibody conjugates, etc. A difference in the binding affinity of the vertebrate UNC-5 protein to the target in the absence of the agent as compared with the binding affinity in the presence of the agent indicates that the agent modulates the binding of the vertebrate UNC-5 protein to the vertebrate UNC-5 binding target. Analogously, in the cell-based transcription assay also described below, a difference in the vertebrate UNC-5 transcriptional induction in the presence and absence of an agent indicates the agent modulates vertebrate UNC-5-induced transcription. A difference, as used herein, is statistically significant and preferably represents at least a 50%, more preferably at least a 90% difference.

The following experimental section and examples are offered by way of illustration and not by way of limitation.

EXPERIMENTAL cDNAs (SEQ ID NOS:1 and 3) encoding two rat homologues of UNC-5, termed UNC5H-1 and UNC5H-2, SEQ ID NOS:5 and 7, respectively, were isolated from an E18 rat brain cDNA library (see Methods). The predicted proteins show sequence similarity with UNC-5 over their entire lengths, but are more similar to one another (52% identity) than to UNC-5 (28% identity in each case). Like UNC-5[14], both possess two predicted Ig-like domains and two predicted thrombospondin type-1 repeats in their extracellular domains (residues 1–332 of SEQ ID NO:5 and 1–334 of SEQ ID NO:7), a predicted membrane spanning region, and a large intracellular domain. The UNC5H proteins also each possess a signal sequence which, curiously, is lacking in UNC-5[14]. The predicted topology of the UNC5H proteins in cell membranes was verified using recombinant versions of the proteins expressed in transfected cells and antibodies directed against the extracellular and intracellular domains (see Methods). The cytoplasmic domains of the two UNC5H proteins do not contain obvious signaling motifs, but do possess a small region of homology to Zona Occludens-1 (ZO-1), a protein that localizes to adherens junctions and is implicated in junction formation[18,19]. ZO-1 contains PDZ-domains[18,19], structures implicated in protein clustering[20], but the region of homology with UNC-5 homologues corresponds to a unique sequence at the carboxy terminus of ZO-1. The homology between ZO-1 and C. elegans UNC-5 is less pronounced (and is not detected by computer BLAST search), but is nonetheless apparent when all four sequences are aligned.

To determine whether the UNC-5 homologues are candidates for receptors involved in neuronal migration or axon guidance, we first examined the sites of expression of Unc5h-1 and Unc5h-2 by RNA in situ hybridization in rat embryos. Unc5h-1 transcripts are detected at early stages of neural tube development in the ventral spinal cord. At embryonic day 11 (E11), when motoneurons are beginning to differentiate in that region[21], transcripts are present throughout the ventral spinal cord, excluding the midline floor plate region, but are most intense in the ventricular zone and at the lateral edges. At E12, prominent expression is observed in the motor columns, but also extends more dorsally, and is now becoming excluded from the ventricular zone. This more dorsal expression appears transient, as expression by E13 is confined to postmitotic cells in the ventral spinal cord, apparently including the motoneurons. Unc5h-2 transcripts are not detected at significant levels in the spinal cord until E14, when they are found in the roofplate region. Unc5h-2 transcripts are, however, detected in developing sensory ganglia that flank the spinal cord, at low levels at E12, and at higher levels by E14. The expression of these two genes is thus observed in regions where differentiating neurons are undergoing axonogenesis, consistent with a possible role in this process.

Expression of these genes is also observed at higher axial levels of the nervous system, as well as in non-neural structures. At E13, Unc5h-1 is expressed in the basal plate (ventral neural tube) in the hindbrain and midbrain, in the developing hypothalamus and thalamus, and in the pallidum. Unc5h-2 expression at this stage is detected in the dorsal aspect of the developing optic cup, the nasal pits, apical ridge of the limb bud, urogenital tubercle, and in restricted regions of the midbrain and caudal diencephalon. By E16, Unc5h-1 mRNA is also detected at high levels in the entorhinal cortex and at lower levels throughout the cortex. Unc5h-2 is also detected at this stage at low levels in the cortex, and at high levels in hypertrophic chondrocytes. Expression of the two homologues persists postnatally, with, at postnatal day 10 (P10), continued expression of both at low levels throughout the cortex, expression of both in distinct patterns in the septal area, and high level expression of Unc5h-1 in the developing hippocampus and entorhinal cortex. In addition, a prominent site of postnatal expression of both genes is in the cerebellum. Both are expressed in the inner granule cell layer, and Unc5h-2 is in addition expressed in the inner aspect of the external germinal layer, where granule cell precursors differentiate prior to migrating to their final destination in the inner granule cell layer[22,23]. Thus, expression of Unc5h-2 in this region is associated with a prominent cell migration event in the developing cerebellum.

Although the expression patterns of the two UNC5H proteins were suggestive of potential roles in cell or axon migration, to obtain more direct evidence implicating them in mediating responses to netrins we tested whether netrin-1 can bind cells expressing these proteins. Transfected monkey kidney COS-1 cells or human embryonic kidney 293 cells expressing either UNC5H-1 or UNC5H-2 showed significant binding of netrin-1 protein above background, as is also observed for transfected cells expressing the netrin receptors DCC and neogenin, but not for transfected cells expressing TAG-1 or L1, two other members of the Ig superfamily[13]. In these experiments, binding was performed in the presence of soluble heparin, which eliminates non-specific binding of netrin-1 to the cells[13] but does not evidently prevent binding to the UNC5 homologues. To verify, in the case of UNC5H-2, that exogenously added heparin is not required for the interaction, we generated a soluble protein comprising the extracellular domain of UNC5H-2 fused to the constant region (Fc) of a human immunogloblin molecule. This UNC5H-2-Fc fusion protein bound transfected 293 cells expressing netrin-1 (some of which remains associated with the surface of these cells[3,10]) in the absence of added heparin but did not show binding to non-transfected cells, nor to cells expressing UNC5H-2 itself, DCC, or neogenin. The UNC5H-2-Fc fusion also did not bind transfected cells expressing F-spondin, an adhesive extracellular matrix protein made by floor plate cells[24], or Semaphorin III, a chemorepellent for sensory axons at the stages that Unc5h-2 is expressed in sensory ganglia[25]. Both of these proteins, like netrin-1, are secreted but partition between cell surfaces and the soluble fraction[24,26]. Thus, the interaction between netrin-1 and UNC5H-2 appears specific, and does not require heparin nor reflect a generalized interaction with proteins that associate non-specifically with cell surfaces.

The affinity of UNC-5 homologues for netrin-1 was estimated in equilibrium binding experiments using netrin (VIoV)-Fc, a fusion of the amino terminal two-thirds of netrin-1 to the constant portion of human IgG[13]. This netrin-1 derivative is bioactive but, unlike netrin-1, does not aggregate at high concentrations, and it binds DCC with a Kd comparable to that of full length netrin-1[13]. Specific binding of netrin (VIoV)-Fc to each of the three UNC5 homologues showed saturation and the binding curves were fitted to the Hill equation, yielding Kd values of 19±0.8 nM and 3.4±1.0 nM for UNC5H1 and UNC5H2 respectively. These values are comparable to the Kd for the DCC-netrin (VIoV-Fc) interaction (~5 nM), and are consistent with the effective dose for the axon outgrowth promoting effects of netrin-1[2,13].

Establishing the involvement of these vertebrate UNC5H proteins in cell migration and axon guidance will require perturbing their functions in vivo. In the meantime, however, our results are at least consistent with such an involvement, as these homologues are expressed by some populations of cells that are undergoing migrations or extending axons. For example, Unc5h1 is expressed by spinal motoneurons, whose axons are repelled in vitro by floor plate cells[27], and whose outgrowth in vitro can be suppressed by netrin-1. It is also expressed in the region of trochlear motoneurons, which can be repelled by netrin-1[4]. Both Unc5h genes are also expressed in the developing cerebellum, which is a site of extensive cell migration.

Although the in vivo functions of the UNC-5 homologues described here remain to be determined, our evidence that vertebrate UNC5H proteins bind netrin-1 provides direct support for the idea that members of this new subfamily of the Ig superfamily are netrin receptors. This idea was first proposed for *C. elegans* UNC-5, based on the findings that unc-5 is required cell-autonomously for dorsal migrations that require the function of the netrin UNC-6[14], and that ectopic expression of unc-5 in neurons that normally project longitudinally or ventrally can steer their axons dorsally[17]. Although consistent with the possibility that UNC-5 is an UNC-6 receptor, these results are also consistent with a role for UNC-5 in modifying the function of a distinct UNC-6 receptor. The possibility of a modifier function was made more plausible by evidence that the DCC homologue UNC-40, which is a putative UNC-6 receptor involved in ventral migrations[11], is expressed by axons that project dorsally and is required for those projections[11,15,16], suggesting that UNC-5 might function by switching an attractive netrin receptor (UNC-40) into a repulsive netrin receptor. However, our results suggest that UNC-5 also functions directly as a netrin receptor. A model in which UNC-40 and UNC-5 can form a receptor complex but UNC-5 can also function alone in transducing the UNC-6 netrin signal provides an explanation for the observation that loss of unc-40 function results in a much less severe phenotype for dorsal migrations than do either loss of unc-5 or loss of unc-6 function[15,16].

Recent studies have demonstrated a remarkable phylogenetic conservation in function of netrin proteins in guiding axons towards a source of netrin at the midline of nervous systems of nematodes, flies and vertebrates[1,7,8,9], as well as a conserved role for members of the DCC subfamily of the Ig superfamily in mediating the axonal responses that underlie those guidance events[11,12,13]. The identification of vertebrate homologues of UNC-5, and the evidence that they are netrin-binding proteins, suggests that the signaling mechanisms through which netrins elicit repulsive responses are also conserved.

Isolation of rat UNC-5 homologues, and in situ hybridization. A search of the human expressed sequence tag (EST) databases revealed a small sequence (Genbank accession number R11880) with distant similarity to the carboxy-terminal portion of UNC-5. The corresponding cDNA fragment, amplified by polymerase chain reaction from an embryonic human brain cDNA library (Stratagene), was used to screen the library, resulting in the isolation of a 3.8 kB cDNA clone comprising all but the first 440 nt of the coding region of the human homologue of UNC5H1. Non-overlapping probes from this cDNA were used to screen an E18 rat brain library (gift of S. Nakanishi), leading to isolation of seven partial and one full length UNC5H1 cDNA and one full length UNC5H2 cDNA. Additional screens of E13 rat dorsal and ventral spinal cord libraries resulted in isolation of a second full length UNC5H2 cDNA as well as a nearly full length UNC5H1 cDNA. Sequencing was performed on a Licor (L4000) automated sequencer as well as by $^{33}$P cycle sequencing. Genbank accession numbers are U87305 and U87306 for rUNC5H1 and rUNC5H2 respectively. RNA in situ hybridization was performed as described[13].

Antibodies, expression constructs and immunohistochemistry. Rabbit polyclonal antisera were raised to a peptide corresponding to a sequence (YLRKNFEQEPLAKE (SEQ ID NO: 10), residues 148–161 of SEQ ID NO:7) in the extracellular domain of UNC5H-2 that is almost completely conserved in UNC5H-1 (one amino acid substitution), and to peptides corresponding to unique sequences in the cytoplasmic domains of UNC5H-1 (GEPSPDSWSLRLKKQ (SEQ ID NO:1 1), residues 580–594 of SEQ ID NO:5 and UNC5H-2 (EARQQDDGDLNSLASA (SEQ ID NO:12), residues 909–924 of SEQ ID NO:7). Antisera were affinity-purified on the respective peptides (Quality Controlled Biochemicals). cDNAs for the various constructs were subcloned into the COS cell expression vector pMT21 and the 293-EBNA cell expression vector pCEP4 (Invitrogen), and transiently transfected into those cells using lipofectamine. The antiserum to the extracellular peptide can detect both UNC5H proteins expressed in transfected cells without cell permeabilization, whereas the antisera directed against the cytoplasmic domain peptides detected their respective proteins after cell permeabilization. Netrin-1 protein (SEQ ID NO:9) was produced, purified, used and visualized in binding assays as described[13], except that a monoclonal antibody (9E10)[29] directed to a C-terminal myc-epitope tag was used to detect recombinant netrin-1, and heparin was used at 1 µg/ml. A 293-EBNA cell line stably expressing the UNC5H-2-Fc fusion was derived and maintained as described[10,13]. The fusion protein was purified from serum-free medium conditioned for seven days by affinity chromatography on protein A agarose. The 293 cell line expressing netrin-1 was as described[13]. Binding of the UNC5H-2-Fc fusion to this line was visualized using a Cy3-conjugated secondary antibody (Jackson Immunoresearch) directed against human Fc.

REFERENCES

1. Ishii, N., et al., *Neuron* 9, 873–81 (1992).
2. Serafini, T. et al. *Cell* 78, 409–24 (1994).
3. Kennedy, T. E., Serafini, T., de la Torre, J. R. & Tessier-Lavigne, M. *Cell* 78, 425–35 (1994).
4. Colamarino, S. A. & Tessier-Lavigne, M. *Cell* 81, 621–9 (1995).
5. Shirasaki, R., Tamada, A., Katsumata, R. & Murakami, F. *Neuron* 14, 961–72 (1995).
6. Wadsworth, W. G., Bhatt, H. & Hedgecock, E. M. *Neuron* 16, 35–46 (1996).
7. Mitchell, K. J., et al., *Neuron* 17, 203 (1996)
8. Harris, R., Sabatelli, L. M. & Seeger, M. A. *Neuron* 17, 217–228 (1996).
9. Serafini, T., et al., *Cell* in press.
10. Shirasaki, R., Mirzayan, C., Tessier-Lavigne, M. & Murakami, F. *Neuron* in press, (1996).
11. ChanS. S. -Y., et al., *Cell* 87, 187–196 (1996).
12. Kolodziej, P. A., et al., *Cell* 87, 197–204 (1996)
13. Keino-Masu, K, et al., *Cell* 87, 175–185 (1996).
14. Leung-Hagesteijn, C. et al. *Cell* 71, 289–99 (1992).
15. Hedgecock, E. M., Culotti, J. G. & Hall, D. H. *Neuron* 4, 61–85 (1990).
16. McIntire, S. L., et al., *Neuron* 8, 307–22 (1992).
17. Hamelin, M., Zhou, Y., Su, M. W., Scott, I. M. & Culotti, J. G. *Nature* 364, 327–30 (1993).
18. Willott E; et al., Proc. *Natl Acad. Sci* 90, 7834–8 (1993).
19. Itoh M; et al., *J. Cell Biol.* 121, 491–502 (1993).
20. Sheng, M. *Neuron* 17, 575–578 (1996).
21. Altman, J., & Bayer, S. A. *Adv. Anat. Embryol. Cell Biol.* 85, 1–166 (1984).
22. Ramon y Cajal, S. *Histologie du Systeme Nerveux de l'Home et des Vertebres*, Vol. 2 (1911).
23. Rakic, P. *J. Comp. Neurol.* 141, 283–312 (1971).
24. Klar A; Baldassare M; & Jessell T M. *Cell* 69, 95–110. (1992).
25. Messersmith, E. K. et al. *Neuron* 14, 949–59 (1995).
26. Luo, Y., Raible, D. & Raper, J. A. *Cell* 75, 217–27 (1993).
27. Guthrie, S. & Pini, A. *Neuron* 14, 1117–30 (1995).
28. Evan, G. I., Lewis, G. K., Ramsey, G., & Bishop, J. M. *Mol. Cell Biol.* 5, 3610–3616 (1985).

EXAMPLES

1. Protocol for high throughput vertebrate UNC-5- netrin binding assay.
   A. Reagents:
   Neutralite Avidin: 20 µg/ml in PBS.
   Blocking buffer: 5% BSA, 0.5% Tween 20 in PBS; 1 hour at room temperature.
   Assay Buffer: 100 mM KCl, 20 mM HEPES pH 7.6, 1 mM MgCl$_2$, 1% glycerol, 0.5% NP-40, 50 mM b-mercaptoethanol, 1 mg/ml BSA, cocktail of protease inhibitors.
   $^{33}$P vertebrate UNC-5 protein 10x stock: $10^{-8-10-6}$ M "cold" vertebrate UNC-5 supplemented with 200,000–250,000 cpm of labeled vertebrate UNC-51 (Beckman counter). Place in the 4° C. microfridge during screening.
   Protease inhibitor cocktail (1000X): 10 mg Trypsin Inhibitor (BMB # 109894), 10 mg Aprotinin (BMB # 236624), 25 mg Benzamidine (Sigma # B-6506), 25 mg Leupeptin (BMB # 1017128), 10 mg APMSF (BMB # 917575), and 2mM NaVo$_3$ (Sigma # S-6508) in 10 ml of PBS.
   nerin-1: $10^{-7-10-5}$M biotinylated netrin-1 in PBS.
   B. Preparation of assay plates:
   Coat with 120 µl of stock N-Avidin per well overnight at 4° C.
   Wash 2 times with 200 µl PBS.
   Block with 150 µl of blocking buffer.
   Wash 2 times with 200 µl PBS.
   C. Assay:
   Add 40 µl assay buffer/well.
   Add 10 µl compound or extract.
   Add 10 µl $^{33}$P-UNC-5 (20–25,000 cpm/0.1–10 µmoles/well=$10^{-9-10-7}$
   Shake at 25° C. for 15 minutes.
   Incubate additional 45 minutes at 25° C.
   Add 40 µM biotinylated netrin-1 (0.1–10 pmoles/40 ul in assay buffer)
   Incubate 1 hour at room temperature.
   Stop the reaction by washing 4 times with 200 µM PBS.
   Add 150 µM scintillation cocktail.
   Count in Topcount.
   D. Controls for all assays (located on each plate):
   a. Non-specific binding
   b. Soluble (non-biotinylated netrin-1) at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated vertebrate UNC-5 protein-specific antibody, wherein the UNC-5 protein consists of a sequence selected from the group consisting of SEQ ID NO:5, 6, 7 and 8.

2. An antibody according to claim 1, wherein the UNC-5 protein consists of SEQ ID NO:5.

3. An antibody according to claim 1, wherein the UNC-5 protein consists of SEQ ID NO:6.

4. An antibody according to claim 1, wherein the UNC-5 protein consists of SEQ ID NO:7.

5. An antibody according to claim 1, wherein the UNC-5 protein consists of SEQ ID NO:8.

6. A method for specifically detecting a vertebrate UNC-5 protein selected from the group consisting of SEQ ID NO:5, 6, 7 and 8, comprising the steps of:
  incubating a sample with an antibody according to claim 1; and
  detecting a resultant specific binding of the antibody to a protein.

7. A method for specifically detecting a vertebrate UNC-5 protein of SEQ ID NO:5, comprising the steps of:
  incubating a sample with an antibody according to claim 2; and
  detecting a resultant specific binding of the antibody to a protein.

8. A method for specifically detecting a vertebrate UNC-5 protein of SEQ ID NO:6, comprising the steps of:
  incubating a sample with an antibody according to claim 3; and
  detecting a resultant specific binding of the antibody to a protein.

9. A method for specifically detecting a vertebrate UNC-5 protein of SEQ ID NO:7, comprising the steps of:
  incubating a sample with an antibody according to claim 4; and
  detecting a resultant specific binding of the antibody to a protein.

10. A method for specifically detecting a vertebrate UNC-5 protein of SEQ ID NO:8, comprising the steps of:
  incubating a sample with an antibody according to claim 5; and
  detecting a resultant specific binding of the antibody to a protein.

11. The antibody of claim 1, wherein the antibody is a polyclonal antibody.

12. The antibody of claim 1, where the antibody is a monoclonal antibody.

13. The antibody of claim 1, labeled with a detectable label.

14. The antibody of claim 13, wherein the label is fluorescent, radioactive or chemiluminescent.

* * * * *

```
                             SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
          (A) LENGTH: 3014 base pairs
          (B) TYPE: nucleic acid
          (C) STRANDEDNESS: double
          (D) TOPOLOGY: linear (ii) MOLECULE TYPE: cDNA (xi) SEQUENCE DESCRIPTION: SEQ ID NO: 1:

ATGGCCGTCC GGCCCGGCCT GTGGCCAGTG CTCCTGGGCA TAGTCCTCGC CGCCTGGCTT      60

CGTGGTTCGG GTGCCCAGCA GAGTGCCACG GTGGCCAATC CAGTGCCCGG TGCCAACCCC     120

GACCTGCTGC CCCACTTCCT GGTAGAGCCT GAGGACGTGT ACATTGTCAA GAACAAGCCG     180

GTGTTGTTGG TGTGCAAGGC TGTGCCTGCC ACCCAGATCT TCTTCAAGTG CAATGGGGAA     240

TGGGTCCGCC AGGTCGATCA CGTAATTGAA CGCAGCACCG ACAGCAGCAG CGGATTGCCA     300

ACCATGGAGG TCCGTATCAA CGTATCGAGG CAGCAGGTAG AGAAAGTGTT TGGGCTGGAG     360

GAATACTGGT GCCAGTGTGT GGCATGGAGC TCCTCGGGTA CCACCAAAAG TCAGAAGGCC     420

TACATCCGGA TTGCCTATTT GCGCAAGAAC TTTGAGCAGG AGCCACTGGC CAAGGAAGTG     480

TCACTGGAGC AAGGCATTGT ACTACCTTGT CGCCCCCCAG AAGGAATCCC CCCAGCTGAG     540

GTGGAGTGGC TTCGAAATGA GGACCTCGTG GACCCCTCCC TCGATCCCAA TGTGTACATC     600

ACGCGGGAGC ACAGCCTAGT CGTGCGTCAG GCCCGCCTGG CCGACACGGC CAACTACACC     660

TGTGTGGCCA AGAACATCGT AGCCCGTCGC CGAAGCACCT CTGCAGCGGT CATTGTTTAT     720

GTGAACGGTG GGTGGTCGAC GTGGACTGAG TGGTCCGTCT GCAGCGCCAG CTGTGGGCGT     780

GGCTGGCAGA AACGGAGCCG GAGCTGCACC AACCCGGCAC CTCTCAACGG GGGCGCCTTC     840

TGTGAGGGGC AGAATGTCCA GAAAACAGCC TGCGCCACTC TGTGCCCAGT GGATGGGAGC     900

TGGAGTTCGT GGAGTAAGTG GTCAGCCTGT GGGCTTGACT GCACCCACTG GCGGAGCCGC     960

GAGTGCTCTG ACCCAGCACC CCGCAATGGA GGTGAGGAGT GTCGGGGTGC TGACCTGGAC    1020

ACCCGCAACT GTACCAGTGA CCTCTGCCTG CACACCGCTT CTTGCCCCGA GGACGTGGCT    1080

CTCTACATCG GCCTTGTCGC TGTGGCTGTG TGCCTCTTCT TGCTGTTGCT GGCCCTTGGA    1140

CTCATTTACT GTCGCAAGAA GGAAGGGCTG GACTCCGATG TGGCCGACTC GTCCATCCTC    1200

ACCTCGGGCT TCCAGCCTGT CAGCATCAAG CCCAGCAAAG CAGACAACCC CCACCTGCTC    1260

ACCATCCAGC CAGACCTCAG CACCACCACT ACCACCTACC AGGGCAGTCT ATGTTCGAGG    1320

CAGGATGGAC CCAGCCCCAA GTTCCAGCTC TCTAATGGTC ACCTGCTCAG CCCACTGGGG    1380

AGTGGCCGCC ATACGTTGCA CCACAGCTCA CCCACCTCTG AGGCTGAGGA CTTCGTCTCC    1440

CGCCTCTCCA CCCAAAACTA CTTTCGTTCC CTGCCCCGCG GCACCAGCAA CATGGCCTAC    1500

GGGACCTTCA ACTTCCTCGG GGGCCGGCTG ATGATCCCTA ATCGGGGGAT CAGCCTCCTC    1560

ATACCCCGG ATGCCATCCC CCGAGGAAAG ATCTACGAGA TCTACCTCAC ACTGCACAAG    1620
```

```
CCAGAAGACG TGAGGTTGCC CCTAGCTGGC TGTCAGACCC TGCTGAGTCC AGTCGTTAGC    1680

TGTGGGCCCC CAGGAGTCCT GCTCACCCGG CCAGTCATCC TTGCAATGGA CCACTGTGGA    1740

GAGCCCAGCC CTGACAGCTG GAGTCTGCGC CTCAAAAAGC AGTCCTGCGA GGGCAGTTGG    1800

GAGGATGTGC TGCACCTTGG TGAGGAGTCA CCTTCCCACC TCTACTACTG CCAGCTGGAG    1860

GCCGGGGCCT GCTATGTCTT CACGGAGCAG CTGGGCCGCT TTGCCCTGGT AGGAGAGGCC    1920

CTCAGCGTGG CTGCCACCAA GCGCCTCAGG CTCCTTCTGT TTGCTCCCGT GGCCTGTACG    1980

TCCCTTGAGT ACAACATCCG AGTGTACTGC CTACACGACA CCCACGACGC TCTCAAGGAG    2040

GTGGTGCAGC TGGAGAAGCA GCTAGGTGGA CAGCTGATCC AGGAGCCTCG CGTCCTGCAC    2100

TTCAAAGACA GTTACCACAA CCTACGTCTC TCCATCCACG ACGTGCCCAG CTCCCTGTGG    2160

AAGAGCAAGC TACTTGTCAG CTACCAGGAG ATCCCTTTTT ACCACATCTG GAACGGCACC    2220

CAGCAGTATC TGCACTGCAC CTTCACCCTG GAGCGCATCA CGCCAGCAC CAGCGACCTG     2280

GCCTGCAAGG TGTGGGTGTG GCAGGTGGAG GGAGATGGGC AGAGCTTCAA CATCAACTTC    2340

AACATCACTA GGACACAAG GTTTGCTGAA TTGTTGGCTC TGGAGAGTGA AGGGGGGGTC     2400

CCAGCCCTGG TGGGCCCCAG TGCCTTCAAG ATCCCCTTCC TCATTCGGCA AAAGATCATC    2460

GCCAGTCTGG ACCCACCCTG CAGCCGGGGC GCCGACTGGA GAACTCTAGC CCAGAAACTT    2520

CACCTGGACA GCCATCTTAG CTTCTTTGCC TCCAAGCCCA GCCCTACAGC CATGATCCTC    2580

AACCTATGGG AGGCACGGCA CTTCCCCAAC GGCAACCTCG GCCAGCTGGC AGCAGCTGTG    2640

GCCGGACTGG GCCAACCAGA TGCTGGCCTC TTCACGGTGT CGGAGGCCGA GTGTTGAGAC    2700

CAGCCAGGCC GGTAATGCCT ACATTCTCAC CAGCTTTGAC ACCTGCCAGG GACAGGCAAA    2760

ACCAGACAGG GGCCCTTCCC CCACACCCGG GGAGAGCTGC TTGGACAGGC CCCTCCTGG    2820

TGAAGTTGTC CCTCGATGCT GGTCCTTCAG ACCCTGCCCA AACTCCATCC CTCCATGGCC    2880

TGCCCGGCCA GGTTGGTCTA GCCACCTGCT CTCACTCTGC CCTGGTCCCA GGGCCAGAGT    2940

AGACAGTCCT GGAGCCTGGG CTGAGCCTCG CCAGCCCATC TGTGTGTGTG TGTATATGCG    3000

TGTATGCTAC CTCT                                                     3014

(2) INFORMATION FOR SEQ ID NO: 2:

(i) SEQUENCE CHARACTERISTICS:
        (A) LENGTH: 1787 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 2:

GCAACTGTAC CAGTGACCTC TGGTACACAC TGCTTCTGGC CCTGAGGACG TGGCCCTCTA      60

TGTGGGCCTC ATCGCCGTGG CCGTCTGCCT GGTCCTGCTG CTGCTTGTCC TCATCCTCGT     120

TTATTGCCGG AAGAAGGAGG GGCTGGACTC AGATGTGGCT GACTCGTCCA TTCTCACCTC     180

AGGCTTCCAG CCCGTCAGCA TCTAAGCCCA GCAAAGCAGA CAACCCCCAT CTGCTCACCA     240

TCCAGCCGGA CCTCAGCACC ACCACCACCA CCTACCAGGG CAGTCTCTGT CCCCGGCAGG     300

ATGGGCCCAG CCCCAAGTTC CAGCTCACCA ATGGGCACCT GCTCAGCCCC CTGGGTGGCG     360

GCCGCCACAC ACTGCACCAC AGCTCTCCCA CCTCTGAGGC CGAGGAGTTC GTCTCCCGCC     420

TCTCCACCCA GAACTACTTC CGCTCCCTGC CCGAGGCAC CAGCAACATG ACCTATGGGA      480

CCTTCAACTT CCTCGGGGGC CGGCTGATGA TCCCTAATAC AGGAATCAGC CTCCTCATCC     540
```

-continued

| | |
|---|---|
| CCCCAGATGC CATACCCCGA GGGAAGATCT ATGAGATCTA CCTCACGCTG CACAAGCCGG | 600 |
| AAGACGTGAG GTTGCCCCTA GCTGGCTGTC AGACCCTGCT GAGTCCCATC GTTAGCTGTG | 660 |
| GACCCCCTGG CGTCCTGCTC ACCCGGCCAG TCATCCTGGC TATGGACCAC TGTGGGGAGC | 720 |
| CCAGCCCTGA CAGCTGGAGC CTGGCCCTCA AAAAGCAGTC GTGCGAGGGA GCTGGGAGGA | 780 |
| TGTCTGCACC TGGGCGAGGA GGCGCCCTCC CACCTCTACT ACTGCCAGCT GGAGGCCAGT | 840 |
| GCCTGCTACG TCTTCACCGA GCAGCTGGGC CGCTTTGCCC TGGTGGGAGA GGCCCTCAGC | 900 |
| GTGGCTGCCG CCAAGCGCCT CAAGCTGCTT CTGTTTGCGC CGGTGGCCTG CACCTCCCTC | 960 |
| GAGTACAACA TCCGGGTCTA CTGCCTGCAT GACACCCACG ATGCACTCAA GGAGGTGGTG | 1020 |
| CAGCTGGAGA AGCAGCTGGG GGGACAGCTG ATCCAGGAGC CACGGGTCCT GCACTTAAGG | 1080 |
| ACAGTTACCA CAACCTGCCC TATCATCCAC GATGTGCCCA GCTCCCTGTG AAGAGTAAG | 1140 |
| CTCCTTGTCA GCTACCAGGA GATCCCCTTT TATCACATCT GGAATGGCAC GCAGCGGTAC | 1200 |
| TTGCACTGCA CCTTCACCCT GGAGCGTGTC AGCCCCAGCA CTAGTGACCT GGCCTGCAAG | 1260 |
| CTGTGGGTGT GGCAGGTGGA GGGCGACGGG CAGAGCTTCA GCATCAACTT CAACATCACC | 1320 |
| AAGGACACAA GGTTTGCTGA GCTGCTGGCT CTGGAGAGTG AAGCGGGGGT CCCAGCCCTG | 1380 |
| GTGGGCCCCA GTGCCTTCAA GATCCCCTTC CTCATTCGGC AGAAGATAAT TTCCAGCCTG | 1440 |
| GACCCACCCT GTAGGCGGGG TGCCGACTGG CGGACTCTGG CCCAGAAACT CCACCTGGAC | 1500 |
| AGCCATCTCA GCTTCTTTGC CTCCAAGCCC AGCCCCACAG CCATGATCCT CAACCTGTGG | 1560 |
| GAGGCGCGGC ACTTCCCCAA CGGCAACCTC AGCCAGCTGG CTGCAGCAGT GGCTGGGACT | 1620 |
| GGCCAGCAGG ACGGTGGCTT CTTTCACAGT GTTCGGAGGC TGAGTGCTGA GGCCGGCCAG | 1680 |
| GCGAACACTA CAATTTTACC AGTTTTGGGA ACCCACCAAG GGACAGGCAG AAGCCGGACA | 1740 |
| AGGGCTTTTC CCAAAACCGG GGAGAGTTTT TTTGGAAAAG GCCTTTT | 1787 |

(2) INFORMATION FOR SEQ ID NO: 3:

(i) SEQUENCE CHARACTERISTICS:
        (A) LENGTH: 2831 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 3:

| | |
|---|---|
| ATGAGGGCCC GGAGCGGCGG GGCCGCTGCT GTGGCGCTGC TGCTCTGCTG GGATCCGACA | 60 |
| CCGAGCTTAG CAGGCATTGA CTCTGGTGCC CAGGGACTCC CAGACTCCTT CCCATCAGCA | 120 |
| CCCGCGGAGC AGCTGCCTCA CTTCCTGCTG GAACCAGAGG ATGCCTACAT CGTAAAGAAC | 180 |
| AAGCCAGTGG AATTGCACTG CCGAGCCTTC CCTGCCACAC AGATCTACTT CAAGTGTAAT | 240 |
| GGCGAGTGGG TTAGCCAGAA AGGCCACGTC ACGCAGGAGA GCCTGGATGA GGCCACAGGC | 300 |
| TTGCGAATAC GAGAGGTGCA GATAGAGGTG TCGCGGCAGC AGGTGGAGGA ACTTTTTGGG | 360 |
| CTCGAGGACT ACTGGTGTCA GTGCGTGGCC TGGAGCTCTT CGGGAACCAC CAAGAGTCGC | 420 |
| CGAGCCTACA TCCGCATTGC CTACTTGCGC AAGAACTTTG ACCAGGAGCC TCTGGCGAAG | 480 |
| GAGGTACCCT TGGATCATGA GGTCCTTCTG CAGTGCCGCC ACCAGAGGG AGTGCCTGTG | 540 |
| GCTGAGGTGG AATGGCTCAA GAATGAAGAT GTCATCGATC CCGCTCAGGA CACTAACTTC | 600 |
| CTGCTCACCA TTGACCACAA CCTCATCATC CGCCAGGCGC GCCTCTCAGA CACAGCCAAC | 660 |
| TACACCTGTG TGGCAAAGAA TATTGTGGCC AAGCGCCGGA GCACGACGGC CACAGTCATC | 720 |

-continued

| | |
|---|---|
| GTCTATGTGA ACGGAGGTTG GTCCAGCTGG GCAGAATGGT CACCCTGCTC TAACCGCTGC | 780 |
| GGCCGAGGTT GGCAGAAACG TACTAGGACC TGCACCAACC CAGCCCCACT CAATGGAGGT | 840 |
| GCCTTCTGCG AGGGACAGGC TTGCCAGAAG ACGGCTTGCA CCACCGTGTG CCCAGTGGAT | 900 |
| GGAGCGTGGA CTGAGTGGAG CAAGTGGTCC GCCTGCAGCA CAGAGTGTGC GCACTGGCGC | 960 |
| AGCCGCGAGT GCATGGCACC GCCGCCCCAG AACGGAGGCC GTGACTGCAG CGGGACGCTA | 1020 |
| CTTGACTCCA AGAACTGCAC CGATGGGCTG TGCGTGCTGA ATCAGAGAAC TCTAAACGAC | 1080 |
| CCTAAAAGCC GCCCCCTGGA GCCGTCGGGA GACGTGGCGC TGTATGCGGG CCTCGTGGTG | 1140 |
| GCCGTCTTTG TGGTTCTGGC AGTTCTCATG GCTGTAGGAG TGATCGTGTA CCGGAGAAAC | 1200 |
| TGCCGGGACT TCGACACGGA CATCACTGAC TCCTCTGCTG CCCTCACTGG TGGTTTCCAC | 1260 |
| CCCGTCAACT TCAAGACTGC AAGGCCCAGC AACCCACAGC TCCTGCACCC ATCCGCCCCT | 1320 |
| CCGGACCTAA CGGCCAGTGC TGGCATCTAC CGCGGACCTG TGTATGCCCT GCAGGACTCT | 1380 |
| GCCGACAAGA TCCCTATGAC TAATTCACCC CTTCTGGATC CCTTGCCCAG CCTCAAGATC | 1440 |
| AAGGTCTATG ACTCCAGCAC CATCGGCTCT GGGGCTGGCC TGGCTGATGG AGCCGACCTG | 1500 |
| CTGGGTGTCT TACCACCCGG TACATACCCA GGCGATTTCT CCCGGGACAC CCACTTCCTG | 1560 |
| CACCTGCGCA GCGCCAGCCT TGGTTCCCAG CACCTCCTGG GCCTCCCTCG AGACCCCAGC | 1620 |
| AGCAGTGTCA GTGGCACCTT TGGTTGCCTG GGTGGGAGGC TGACCATTCC CGGCACAGGG | 1680 |
| GTCAGCCTGT TGGTACCAAA TGGAGCCATT CCCCAGGGCA AGTTCTATGA CTTGTATCTA | 1740 |
| CGTATCAACA AGACTGAAAG CACCCTCCCA CTTTCGGAAG GTTCCCAGAC AGTATTGAGC | 1800 |
| CCCTCGGTGA CCTGCGGGCC CACGGGCCTC CTCCTGTGCC GCCCTGTTGT CCTCACTGTG | 1860 |
| CCCCACTGTG CTGAAGTCAT TGCCGGAGAC TGGATCTTCC AGCTCAAGAC CCAGGCCCAT | 1920 |
| CAGGGCCACT GGGAGGAGGT GGTGACTTTG GATGAGGAGA CTCTGAACAC CCCCTGCTAC | 1980 |
| TGCCAGCTAG AGGCTAAATC CTGCCACATC CTGTTGGACC AGCTGGGTAC CTACGTGTTC | 2040 |
| ACGGGCGAGT CCTACTCCCG CTCCGCAGTC AAGCGGCTCC AGCTAGCCAT CTTCGCCCCA | 2100 |
| GCCCTCTGCA CCTCCCTGGA GTATAGTCTC AGGGTCTACT GTCTGGAGGA CACTCCTGCA | 2160 |
| GCACTGAAGG AGGTCCTAGA GCTGGAGAGG ACTCTGGGTG CTACTTGGT GGAGGAGCCC | 2220 |
| AAGACTTTGC TCTTTAAGGA CAGTTACCAC AACCTACGCT CTCCCTCCAT GACATCCCCC | 2280 |
| ATGCCCACTG GAGGAGCAAA CTACTGGCCA AGTACCAGGA GATTCCCTTC TACCATGTGT | 2340 |
| GGAACGGCAG CCAGAAAGCC CTGCACTGCA CTTTCACCCT GGAGAGACAT AGCCTAGCCT | 2400 |
| CCACTGAGTT CACCTGTAAG GTCTGCGTGC GGCAGGTAGA AGGGGAAGGC CAGATTTTCC | 2460 |
| AGCTGCACAC CACGCTGGCT GAGACGCCTG CTGGCTCCCT GGATGCACTC TGCTCTGCCC | 2520 |
| CTGGCAATGC TGCCACCACA CAGCTGGGAC CCTATGCCTT CAAGATACCA CTGTCCATCC | 2580 |
| GCCAGAAGAT CTGCAACAGC CTGGACGCCC CCAACTCACG GGGCAATGAC TGGCGGCTGT | 2640 |
| TGGCACAGAA GCTCTCCATG GACCGGTACC TGAACTACTT CGCCACCAAA GCTAGTCCCA | 2700 |
| CAGGCGTGAT CTTAGACCTC TGGGAAGCTC GGCAGCAGGA TGATGGGAC CTCAACAGCC | 2760 |
| TGGCCAGTGC CTTGGAGGAG ATGGGCAAGA GTGAGATGCT GGTAGCCATG ACCACTGATG | 2820 |
| GCGATTGCTG A | 2831 |

(2) INFORMATION FOR SEQ ID NO: 4:

(i) SEQUENCE CHARACTERISTICS:
        (A) LENGTH: 305 base pairs
        (B) TYPE: nucleic acid
        (C) STRANDEDNESS: double -continued (D) TOPOLOGY: linear (ii) MOLECULE TYPE: cDNA (xi) SEQUENCE DESCRIPTION: SEQ ID NO: 4:

TGGATGAGGA GACCCTGAAC ACACCCTGCT ACTGCAGCTG GAGCCCAGGG CCTGTACATC      60

CTGCTGGACC AGCTGGGCAC CTACGTTTTC ACGGGCGAGT CCTATTCCCG CTCAGCAGTC     120

AAGCGGCTCC AGCTGGCCGT TTCGCCCCCG CCCTCTGCAC CTCCCTGGAG TACAGCCTCC     180

GGGTCTACTG CCTGGAGGAC ACGCCTGTAG CACTGAAGGA GGTGCTGGAG CTGGAGCGGA     240

CTCTGGGCGG ATACTTGGTG GAGGAGCCGA AACCGCTAAT GTTCAAGGAC AGTTACCACA     300

ACCTT                                                                305

(2) INFORMATION FOR SEQ ID NO: 5:

(i) SEQUENCE CHARACTERISTICS:
        (A) LENGTH: 898 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO: 5:

Met Ala Val Arg Pro Gly Leu Trp Pro Val Leu Leu Gly Ile Val Leu
1               5                   10                  15

Ala Ala Trp Leu Arg Gly Ser Gly Ala Gln Gln Ser Ala Thr Val Ala
            20                  25                  30

Asn Pro Val Pro Gly Ala Asn Pro Asp Leu Leu Pro His Phe Leu Val
        35                  40                  45

Glu Pro Glu Asp Val Tyr Ile Val Lys Asn Lys Pro Val Leu Leu Val
    50                  55                  60

Cys Lys Ala Val Pro Ala Thr Gln Ile Phe Phe Lys Cys Asn Gly Glu
65                  70                  75                  80

Trp Val Arg Gln Val Asp His Val Ile Glu Arg Ser Thr Asp Ser Ser
                85                  90                  95

Ser Gly Leu Pro Thr Met Glu Val Arg Ile Asn Val Ser Arg Gln Gln
            100                 105                 110

Val Glu Lys Val Phe Gly Leu Glu Glu Tyr Trp Cys Gln Cys Val Ala
        115                 120                 125

Trp Ser Ser Ser Gly Thr Thr Lys Ser Gln Lys Ala Tyr Ile Arg Ile
    130                 135                 140

Ala Tyr Leu Arg Lys Asn Phe Glu Gln Glu Pro Leu Ala Lys Glu Val
145                 150                 155                 160

Ser Leu Glu Gln Gly Ile Val Leu Pro Cys Arg Pro Pro Glu Gly Ile
                165                 170                 175

Pro Pro Ala Glu Val Glu Trp Leu Arg Asn Glu Asp Leu Val Asp Pro
            180                 185                 190

Ser Leu Asp Pro Asn Val Tyr Ile Thr Arg Glu His Ser Leu Val Val
        195                 200                 205

Arg Gln Ala Arg Leu Ala Asp Thr Ala Asn Tyr Thr Cys Val Ala Lys
    210                 215                 220

Asn Ile Val Ala Arg Arg Arg Ser Thr Ser Ala Ala Val Ile Val Tyr
225                 230                 235                 240

Val Asn Gly Gly Trp Ser Thr Trp Thr Glu Trp Ser Val Cys Ser Ala
                245                 250                 255

```
Ser Cys Gly Arg Gly Trp Gln Lys Arg Ser Arg Ser Cys Thr Asn Pro
            260                 265                 270

Ala Pro Leu Asn Gly Gly Ala Phe Cys Glu Gly Gln Asn Val Gln Lys
            275                 280                 285

Thr Ala Cys Ala Thr Leu Cys Pro Val Asp Gly Ser Trp Ser Ser Trp
            290                 295                 300

Ser Lys Trp Ser Ala Cys Gly Leu Asp Cys Thr His Trp Arg Ser Arg
305                 310                 315                 320

Glu Cys Ser Asp Pro Ala Pro Arg Asn Gly Gly Glu Cys Arg Gly
                325                 330                 335

Ala Asp Leu Asp Thr Arg Asn Cys Thr Ser Asp Leu Cys Leu His Thr
            340                 345                 350

Ala Ser Cys Pro Glu Asp Val Ala Leu Tyr Ile Gly Leu Val Ala Val
            355                 360                 365

Ala Val Cys Leu Phe Leu Leu Leu Ala Leu Gly Leu Ile Tyr Cys
            370                 375                 380

Arg Lys Lys Glu Gly Leu Asp Ser Asp Val Ala Asp Ser Ser Ile Leu
385                 390                 395                 400

Thr Ser Gly Phe Gln Pro Val Ser Ile Lys Pro Ser Lys Ala Asp Asn
            405                 410                 415

Pro His Leu Leu Thr Ile Gln Pro Asp Leu Ser Thr Thr Thr Thr Thr
            420                 425                 430

Tyr Gln Gly Ser Leu Cys Ser Arg Gln Asp Gly Pro Ser Pro Lys Phe
            435                 440                 445

Gln Leu Ser Asn Gly His Leu Leu Ser Pro Leu Gly Ser Gly Arg His
            450                 455                 460

Thr Leu His His Ser Ser Pro Thr Ser Glu Ala Glu Asp Phe Val Ser
465                 470                 475                 480

Arg Leu Ser Thr Gln Asn Tyr Phe Arg Ser Leu Pro Arg Gly Thr Ser
                485                 490                 495

Asn Met Ala Tyr Gly Thr Phe Asn Phe Leu Gly Gly Arg Leu Met Ile
            500                 505                 510

Pro Asn Thr Gly Ile Ser Leu Leu Ile Pro Pro Asp Ala Ile Pro Arg
            515                 520                 525

Gly Lys Ile Tyr Glu Ile Tyr Leu Thr Leu His Lys Pro Glu Asp Val
            530                 535                 540

Arg Leu Pro Leu Ala Gly Cys Gln Thr Leu Leu Ser Pro Val Val Ser
545                 550                 555                 560

Cys Gly Pro Pro Gly Val Leu Leu Thr Arg Pro Val Ile Leu Ala Met
                565                 570                 575

Asp His Cys Gly Glu Pro Ser Pro Asp Ser Trp Ser Leu Arg Leu Lys
            580                 585                 590

Lys Gln Ser Cys Glu Gly Ser Trp Glu Asp Val Leu His Leu Gly Glu
            595                 600                 605

Glu Ser Pro Ser His Leu Tyr Tyr Cys Gln Leu Glu Ala Gly Ala Cys
            610                 615                 620

Tyr Val Phe Thr Glu Gln Leu Gly Arg Phe Ala Leu Val Gly Glu Ala
625                 630                 635                 640

Leu Ser Val Ala Ala Thr Lys Arg Leu Arg Leu Leu Phe Ala Pro
                645                 650                 655

Val Ala Cys Thr Ser Leu Glu Tyr Asn Ile Arg Val Tyr Cys Leu His
            660                 665                 670

Asp Thr His Asp Ala Leu Lys Glu Val Val Gln Leu Glu Lys Gln Leu
```

```
                        675                 680                 685
Gly Gly Gln Leu Ile Gln Glu Pro Arg Val Leu His Phe Lys Asp Ser
            690                 695                 700
Tyr His Asn Leu Arg Leu Ser Ile His Asp Val Pro Ser Ser Leu Trp
705                 710                 715                 720
Lys Ser Lys Leu Leu Val Ser Tyr Gln Glu Ile Pro Phe Tyr His Ile
                725                 730                 735
Trp Asn Gly Thr Gln Gln Tyr Leu His Cys Thr Phe Thr Leu Glu Arg
            740                 745                 750
Ile Asn Ala Ser Thr Ser Asp Leu Ala Cys Lys Val Trp Val Trp Gln
            755                 760                 765
Val Glu Gly Asp Gly Gln Ser Phe Asn Ile Asn Phe Asn Ile Thr Lys
770                 775                 780
Asp Thr Arg Phe Ala Glu Leu Leu Ala Leu Glu Ser Glu Gly Gly Val
785                 790                 795                 800
Pro Ala Leu Val Gly Pro Ser Ala Phe Lys Ile Pro Phe Leu Ile Arg
                805                 810                 815
Gln Lys Ile Ile Ala Ser Leu Asp Pro Pro Cys Ser Arg Gly Ala Asp
            820                 825                 830
Trp Arg Thr Leu Ala Gln Lys Leu His Leu Asp Ser His Leu Ser Phe
            835                 840                 845
Phe Ala Ser Lys Pro Ser Pro Thr Ala Met Ile Leu Asn Leu Trp Glu
850                 855                 860
Ala Arg His Phe Pro Asn Gly Asn Leu Gly Gln Leu Ala Ala Ala Val
865                 870                 875                 880
Ala Gly Leu Gly Gln Pro Asp Ala Gly Leu Phe Thr Val Ser Glu Ala
                885                 890                 895
Glu Cys (2) INFORMATION FOR SEQ ID NO: 6:

(i) SEQUENCE CHARACTERISTICS:
        (A) LENGTH: 557 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO: 6:

Asn Cys Thr Ser Asp Leu Xaa Val His Thr Ala Ser Gly Pro Glu Asp
1               5                   10                  15
Val Ala Leu Tyr Val Gly Leu Ile Ala Val Ala Val Cys Leu Val Leu
                20                  25                  30
Leu Leu Leu Val Leu Ile Leu Val Tyr Cys Arg Lys Lys Glu Gly Leu
            35                  40                  45
Asp Ser Asp Val Ala Asp Ser Ser Ile Leu Thr Ser Gly Phe Gln Pro
    50                  55                  60
Val Ser Ile Lys Pro Ser Lys Ala Asp Asn Pro His Leu Leu Thr Ile
65                  70                  75                  80
Gln Pro Asp Leu Ser Thr Thr Thr Thr Tyr Gln Gly Ser Leu Cys
                85                  90                  95
Pro Arg Gln Asp Gly Pro Ser Pro Lys Phe Gln Leu Thr Asn Gly His
            100                 105                 110
Leu Leu Ser Pro Leu Gly Gly Gly Arg His Thr Leu His His Ser Ser
        115                 120                 125
```

```
Pro Thr Ser Glu Ala Glu Phe Val Ser Arg Leu Ser Thr Gln Asn
    130                 135                 140

Tyr Phe Arg Ser Leu Pro Arg Gly Thr Ser Asn Met Thr Tyr Gly Thr
145                 150                 155                 160

Phe Asn Phe Leu Gly Gly Arg Leu Met Ile Pro Asn Thr Gly Ile Ser
                165                 170                 175

Leu Leu Ile Pro Pro Asp Ala Ile Pro Arg Gly Lys Ile Tyr Glu Ile
            180                 185                 190

Tyr Leu Thr Leu His Lys Pro Glu Asp Val Arg Leu Pro Leu Ala Gly
        195                 200                 205

Cys Gln Thr Leu Leu Ser Pro Ile Val Ser Cys Gly Pro Pro Gly Val
    210                 215                 220

Leu Leu Thr Arg Pro Val Ile Leu Ala Met Asp His Cys Gly Glu Pro
225                 230                 235                 240

Ser Pro Asp Ser Trp Ser Leu Ala Leu Lys Lys Gln Ser Cys Glu Gly
                245                 250                 255

Ser Trp Glu Asp Val Leu His Leu Gly Glu Glu Ala Pro Ser His Leu
            260                 265                 270

Tyr Tyr Cys Gln Leu Glu Ala Ser Ala Cys Tyr Val Phe Thr Glu Gln
        275                 280                 285

Leu Gly Arg Phe Ala Leu Val Gly Glu Ala Leu Ser Val Ala Ala Ala
    290                 295                 300

Lys Arg Leu Lys Leu Leu Leu Phe Ala Pro Val Ala Cys Thr Ser Leu
305                 310                 315                 320

Glu Tyr Asn Ile Arg Val Tyr Cys Leu His Asp Thr His Asp Ala Leu
                325                 330                 335

Lys Glu Val Val Gln Leu Glu Lys Gln Leu Gly Gly Gln Leu Ile Gln
            340                 345                 350

Glu Pro Arg Val Leu His Leu Xaa Asp Ser Tyr His Asn Leu Xaa Leu
        355                 360                 365

Ser Xaa His Asp Val Pro Ser Ser Leu Trp Lys Ser Lys Leu Leu Val
    370                 375                 380

Ser Tyr Gln Glu Ile Pro Phe Tyr His Ile Trp Asn Gly Thr Gln Arg
385                 390                 395                 400

Tyr Leu His Cys Thr Phe Thr Leu Glu Arg Val Ser Pro Ser Thr Ser
                405                 410                 415

Asp Leu Ala Cys Lys Leu Trp Val Trp Gln Val Glu Gly Asp Gly Gln
            420                 425                 430

Ser Phe Ser Ile Asn Phe Asn Ile Thr Lys Asp Thr Arg Phe Ala Glu
        435                 440                 445

Leu Leu Ala Leu Glu Ser Glu Ala Gly Val Pro Ala Leu Val Gly Pro
    450                 455                 460

Ser Ala Phe Lys Ile Pro Phe Leu Ile Arg Gln Lys Ile Ile Ser Ser
465                 470                 475                 480

Leu Asp Pro Pro Cys Arg Arg Gly Ala Asp Trp Arg Thr Leu Ala Gln
                485                 490                 495

Lys Leu His Leu Asp Ser His Leu Ser Phe Phe Ala Ser Lys Pro Ser
            500                 505                 510

Pro Thr Ala Met Ile Leu Asn Leu Trp Glu Ala Arg His Phe Pro Asn
        515                 520                 525

Gly Asn Leu Ser Gln Leu Ala Ala Ala Val Ala Gly Thr Xaa Pro Ala
    530                 535                 540
```

```
Gly Arg Trp Leu Leu Ser Gln Cys Ser Glu Ala Glu Cys
545                 550                 555
```

(2) INFORMATION FOR SEQ ID NO: 7:

(i) SEQUENCE CHARACTERISTICS:
        (A) LENGTH: 943 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO: 7:

```
Met Arg Ala Arg Ser Gly Gly Ala Ala Ala Val Ala Leu Leu Leu Cys
1               5                   10                  15

Trp Asp Pro Thr Pro Ser Leu Ala Gly Ile Asp Ser Gly Ala Gln Gly
                20                  25                  30

Leu Pro Asp Ser Phe Pro Ser Ala Pro Ala Glu Gln Leu Pro His Phe
            35                  40                  45

Leu Leu Glu Pro Glu Asp Ala Tyr Ile Val Lys Asn Lys Pro Val Glu
50                  55                  60

Leu His Cys Arg Ala Phe Pro Ala Thr Gln Ile Tyr Phe Lys Cys Asn
65                  70                  75                  80

Gly Glu Trp Val Ser Gln Lys Gly His Val Thr Gln Glu Ser Leu Asp
                85                  90                  95

Glu Ala Thr Gly Leu Arg Ile Arg Glu Val Gln Ile Glu Val Ser Arg
                100                 105                 110

Gln Gln Val Glu Glu Leu Phe Gly Leu Glu Asp Tyr Trp Cys Gln Cys
            115                 120                 125

Val Ala Trp Ser Ser Ser Gly Thr Thr Lys Ser Arg Arg Ala Tyr Ile
130                 135                 140

Arg Ile Ala Tyr Leu Arg Lys Asn Phe Asp Gln Glu Pro Leu Ala Lys
145                 150                 155                 160

Glu Val Pro Leu Asp His Glu Val Leu Leu Gln Cys Arg Pro Pro Glu
                165                 170                 175

Gly Val Pro Val Ala Glu Val Glu Trp Leu Lys Asn Glu Asp Val Ile
                180                 185                 190

Asp Pro Ala Gln Asp Thr Asn Phe Leu Leu Thr Ile Asp His Asn Leu
            195                 200                 205

Ile Ile Arg Gln Ala Arg Leu Ser Asp Thr Ala Asn Tyr Thr Cys Val
210                 215                 220

Ala Lys Asn Ile Val Ala Lys Arg Arg Ser Thr Thr Ala Thr Val Ile
225                 230                 235                 240

Val Tyr Val Asn Gly Gly Trp Ser Ser Trp Ala Glu Trp Ser Pro Cys
                245                 250                 255

Ser Asn Arg Cys Gly Arg Gly Trp Gln Lys Arg Thr Arg Thr Cys Thr
                260                 265                 270

Asn Pro Ala Pro Leu Asn Gly Gly Ala Phe Cys Glu Gly Gln Ala Cys
            275                 280                 285

Gln Lys Thr Ala Cys Thr Thr Val Cys Pro Val Asp Gly Ala Trp Thr
            290                 295                 300

Glu Trp Ser Lys Trp Ser Ala Cys Ser Thr Glu Cys Ala His Trp Arg
305                 310                 315                 320

Ser Arg Glu Cys Met Ala Pro Pro Gln Asn Gly Gly Arg Asp Cys
                325                 330                 335
```

```
Ser Gly Thr Leu Leu Asp Ser Lys Asn Cys Thr Asp Gly Leu Cys Val
        340                 345                 350

Leu Asn Gln Arg Thr Leu Asn Asp Pro Lys Ser Arg Pro Leu Glu Pro
        355                 360                 365

Ser Gly Asp Val Ala Leu Tyr Ala Gly Leu Val Ala Val Phe Val
        370                 375                 380

Val Leu Ala Val Leu Met Ala Val Gly Val Ile Val Tyr Arg Arg Asn
385                     390                 395                 400

Cys Arg Asp Phe Asp Thr Asp Ile Thr Asp Ser Ser Ala Ala Leu Thr
                405                 410                 415

Gly Gly Phe His Pro Val Asn Phe Lys Thr Ala Arg Pro Ser Asn Pro
                420                 425                 430

Gln Leu Leu His Pro Ser Ala Pro Pro Asp Leu Thr Ala Ser Ala Gly
                435                 440                 445

Ile Tyr Arg Gly Pro Val Tyr Ala Leu Gln Asp Ser Ala Asp Lys Ile
        450                 455                 460

Pro Met Thr Asn Ser Pro Leu Leu Asp Pro Leu Pro Ser Leu Lys Ile
465                     470                 475                 480

Lys Val Tyr Asp Ser Ser Thr Ile Gly Ser Gly Ala Gly Leu Ala Asp
                485                 490                 495

Gly Ala Asp Leu Leu Gly Val Leu Pro Pro Gly Thr Tyr Pro Gly Asp
                500                 505                 510

Phe Ser Arg Asp Thr His Phe Leu His Leu Arg Ser Ala Ser Leu Gly
                515                 520                 525

Ser Gln His Leu Leu Gly Leu Pro Arg Asp Pro Ser Ser Ser Val Ser
        530                 535                 540

Gly Thr Phe Gly Cys Leu Gly Gly Arg Leu Thr Ile Pro Gly Thr Gly
545                     550                 555                 560

Val Ser Leu Leu Val Pro Asn Gly Ala Ile Pro Gln Gly Lys Phe Tyr
                565                 570                 575

Asp Leu Tyr Leu Arg Ile Asn Lys Thr Glu Ser Thr Leu Pro Leu Ser
                580                 585                 590

Glu Gly Ser Gln Thr Val Leu Ser Pro Ser Val Thr Cys Gly Pro Thr
        595                 600                 605

Gly Leu Leu Leu Cys Arg Pro Val Val Leu Thr Val Pro His Cys Ala
        610                 615                 620

Glu Val Ile Ala Gly Asp Trp Ile Phe Gln Leu Lys Thr Gln Ala His
625                     630                 635                 640

Gln Gly His Trp Glu Glu Val Val Thr Leu Asp Glu Thr Leu Asn
                645                 650                 655

Thr Pro Cys Tyr Cys Gln Leu Glu Ala Lys Ser Cys His Ile Leu Leu
                660                 665                 670

Asp Gln Leu Gly Thr Tyr Val Phe Thr Gly Glu Ser Tyr Ser Arg Ser
        675                 680                 685

Ala Val Lys Arg Leu Gln Leu Ala Ile Phe Ala Pro Ala Leu Cys Thr
        690                 695                 700

Ser Leu Glu Tyr Ser Leu Arg Val Tyr Cys Leu Glu Asp Thr Pro Ala
705                     710                 715                 720

Ala Leu Lys Glu Val Leu Glu Leu Glu Arg Thr Leu Gly Gly Tyr Leu
                725                 730                 735

Val Glu Glu Pro Lys Thr Leu Leu Phe Lys Asp Ser Tyr His Asn Leu
                740                 745                 750

Arg Leu Ser Leu His Asp Ile Pro His Ala His Trp Arg Ser Lys Leu
```

```
                755             760             765
Leu Ala Lys Tyr Gln Glu Ile Pro Phe Tyr His Val Trp Asn Gly Ser
770                     775                 780

Gln Lys Ala Leu His Cys Thr Phe Thr Leu Glu Arg His Ser Leu Ala
785                 790                 795                 800

Ser Thr Glu Phe Thr Cys Lys Val Cys Val Arg Gln Val Glu Gly Glu
                805                 810                 815

Gly Gln Ile Phe Gln Leu His Thr Thr Leu Ala Glu Thr Pro Ala Gly
                820                 825                 830

Ser Leu Asp Ala Leu Cys Ser Ala Pro Gly Asn Ala Ala Thr Thr Gln
            835                 840                 845

Leu Gly Pro Tyr Ala Phe Lys Ile Pro Leu Ser Ile Arg Gln Lys Ile
850                     855                 860

Cys Asn Ser Leu Asp Ala Pro Asn Ser Arg Gly Asn Asp Trp Arg Leu
865                 870                 875                 880

Leu Ala Gln Lys Leu Ser Met Asp Arg Tyr Leu Asn Tyr Phe Ala Thr
                885                 890                 895

Lys Ala Ser Pro Thr Gly Val Ile Leu Asp Leu Trp Glu Ala Arg Gln
                900                 905                 910

Gln Asp Asp Gly Asp Leu Asn Ser Leu Ala Ser Ala Leu Glu Glu Met
            915                 920                 925

Gly Lys Ser Glu Met Leu Val Ala Met Thr Thr Asp Gly Asp Cys
930                     935                 940

(2) INFORMATION FOR SEQ ID NO: 8:

(i) SEQUENCE CHARACTERISTICS:
        (A) LENGTH: 102 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO: 8:

Asp Glu Glu Thr Leu Asn Thr Pro Cys Tyr Xaa Gln Leu Glu Pro Arg
1               5                   10                  15

Ala Cys Xaa Ile Leu Leu Asp Gln Leu Gly Thr Tyr Val Phe Thr Gly
            20                  25                  30

Glu Ser Tyr Ser Arg Ser Ala Val Lys Arg Leu Gln Leu Ala Val Phe
                35                  40                  45

Ala Pro Ala Leu Cys Thr Ser Leu Glu Tyr Ser Leu Arg Val Tyr Cys
        50                  55                  60

Leu Glu Asp Thr Pro Val Ala Leu Lys Glu Val Leu Glu Leu Glu Arg
65                  70                  75                  80

Thr Leu Gly Gly Tyr Leu Val Glu Glu Pro Lys Pro Leu Met Phe Lys
                85                  90                  95

Asp Ser Tyr His Asn Leu
            100
```